United States Patent
Bao et al.

(10) Patent No.: US 9,915,651 B2
(45) Date of Patent: Mar. 13, 2018

(54) NANOCRYSTAL BASED BIOMOLECULE DETECTION

(71) Applicants: Gang Bao, Mableton, GA (US); Sheng Tong, Atlanta, GA (US)

(72) Inventors: Gang Bao, Mableton, GA (US); Sheng Tong, Atlanta, GA (US)

(*) Notice: Subject to any disclaimer, the term of this patent is extended or adjusted under 35 U.S.C. 154(b) by 1267 days.

(21) Appl. No.: 13/869,780

(22) Filed: Apr. 24, 2013

(65) Prior Publication Data

US 2014/0322818 A1    Oct. 30, 2014

(51) Int. Cl.
   *G01N 33/553*    (2006.01)
   *G01N 33/543*    (2006.01)
   *G01N 33/58*     (2006.01)

(52) U.S. Cl.
   CPC ..... *G01N 33/54306* (2013.01); *G01N 33/553* (2013.01); *G01N 33/588* (2013.01)

(58) Field of Classification Search
   USPC ........................................ 436/524, 525, 526
   See application file for complete search history.

(56) References Cited

U.S. PATENT DOCUMENTS 7,153,703 B2 * 12/2006 Peng ................. C01B 19/007
                                          436/524
7,297,494 B2 * 11/2007 Bao ......................... B82Y 5/00
                                          435/6.1
7,459,145 B2 * 12/2008 Bao ................... A61K 49/0002
                                          424/1.11

OTHER PUBLICATIONS

Teja et al, "Synthesis, properties, and applications of magnetic iron oxide nanoparticles", Progress in Crystal Growth and Characterization of Materials, 55, 2009, pp. 22-45.*
Anthony et al, Handbook of Mineralogy, 2001.*
Alivisatos, "The use of nanocrystals in biological detection", Nat. Biotechnol., 22:47-52 (2004).
Bronstein, et al., "Nanoparticles by decomposition of long chain iron carboxylates: from spheres to stars and cubes", Langmuir, 27:3044-50 (2011).
Burtea, et al., "C-MALISA (cellular magnetic-linked immunosorbent assay), a new application of cellular ELISA for MRI", J. Inorg. Biochem., 99:1135-44 (2005).
Caruntu, et al., "Synthesis of variable-sized nanocrystals of Fe O with high surface activity", Chem. Mater., 16:5527-34 (2004).
Chin, et al., "Microfluidics-based diagnostics of infectious diseases in the developing world", Nat. Med., 17:1015-9 (2011).

(Continued)

*Primary Examiner* — Chris L Chin
(74) *Attorney, Agent, or Firm* — Smith, Gambrell & Russell, LLP; Charles Vorndran

(57) ABSTRACT

A new signal amplification method exploiting the dense atom packing in metallic nanocrystals has been developed for detecting target substances. By dissolving nanocrystals to individual ions that are stoichiometrically converted to chromophores and quantified photometrically, extremely high signal amplification can be achieved. Signal amplification is fully determined by the total number of atoms in the nanocrystals bound to a single target molecule. The disclosed nanocrystal amplification method can be implemented with a rich selection of metal/metal oxide nanocrystals and metal-reactive chromogenic substrates. The chromogenic reactions can be either solution-based or surface-based and performed in aqueous or organic phase, supporting a variety of assay formats.

12 Claims, 15 Drawing Sheets

C. Nanocrystal amplification

(56) References Cited

OTHER PUBLICATIONS

Dykman and Khlebtsov, "Gold nanoparticles in biomedical applications: recent advances and perspectives", Chemical Society Reviews, 41:2256-82 (2012).
Engvall and Perlmann, "Enzyme-linked immunosorbent assay (ELISA). Quantitative assay of immunoglobulin G", Immunochemistry, 8:871-4 (1971).
Gao, et al., "Intrinsic peroxidase-like activity of ferromagnetic nanoparticles", Nat. Nanotechnol., 2:577-83 (2007).
Holliger and Hudson, "Engineered antibody fragments and the rise of single domains", Nature Biotech.nol, 23(9):1126-36 (2005).
Hou, et al., "Controlled synthesis and chemical conversions of FeO nanoparticles", Angewandte Chem Intl Ed., 46:6329-32 (2007).
Huston, et al., "Protein engineering of antibody binding sites: recovery of specific activity in an anti-digoxin single-chain Fv analogue produced in *Escherichia coli*", PNAS, 85:5879-83 (1988).
Jana, et al., "Size and shape controlled magnetic (Cr,Mn,Fe, Co,Ni) oxide nanocrystals via a simple and general approach", Chem. Mater., 16:3931-5 (2004).
Jun, et al., "Nanoscale size effect of magnetic nanocrystals and their utilization for cancer diagnosis via magnetic resonance imaging", J Am Chem. Soc., 127:5732-3 (2005).
Krishnan, et al., "Nanomagnetism and spin electronics: materials, microstructure and novel properties", J. Mater. Sci., 41:793-815 (2006).
Kundra, et al., "Spectrophotometric determination of copper(I) and cobalt(II) with ferrozine", Analytical Chem., 46:1605-6 (1974).
Lin, et al., "Ethylene glycol-protected magnetic nanoparticles for a multiplexed immunoassay in human plasma", Small, 2:485-9 (2006).
Merkoci, et al., "Toward an ICPMS-linked DNA assay based on gold nanoparticles immunoconnected through peptide sequences", Analytical Chemistry, 77:6500-3 (2005).
Nam, et al., "Bio-bar-code-based DNA detection with PCR-like sensitivity", J. Am. Chem. Soc., 126:5932-3 (2004).
Nam, et al., "Nanoparticle-based bio-bar codes for the ultrasensitive detection of proteins", Science, 301:1884-6 (2003).
Nelson, et al., "Development trends for therapeutic antibody fragments", Nat Biotechnol., 27(4):331-7 (2009).
Park, et al., "Ultra-large-scale syntheses of monodisperse nanocrystals", Nat Mater., 3:891-5 (2004).
Peng and Miller, "Recent advancements in optical DNA biosensors: exploiting the plasmonic effects of metal nanoparticles", The Analyst, 136:436-47 (2011).
Perez, et al., "Magnetic relaxation switches capable of sensing molecular interactions", Nat. Biotechnol., 20:816-20 (2002).
Poizot, et al., "Nano-sized transition-metal oxides as negative-electrode materials for lithium-ion batteries", Nature, 407:496-9 (2000).
Quinn, et al., "Simultaneous determination of proteins using an element-tagged immunoassay coupled with ICP-MS detection", J. Anal. Atom Spectrom. 17:892-6 (2002).
Schupbach, "Measurement of HIV-1 p24 antigen by signal-amplification-boosted ELISA of heat-denatured plasma is a simple and inexpensive alternative to tests for viral RNA", AIDS Rev., 4:83-92 (2002).
Stookey, "Ferrozine—a new spectrophotometric reagent for iron", Analytical Chem., 42:779-81 (1970).
Sun, et al., Monodisperse $MFe_2O_4$ (M=Fe, Co, Mn) nanoparticles J. Am. Chem. Soc., 126:273-9 (2004).
Sun, et al., "Tuning exchange bias in core/shell $FeO/Fe_3O_4$ nanoparticles", Nano. Lett., 12:246-51 (2012).
Tong, et al., "Self-assembly of phospholipid-PEG coating on nanoparticles through dual solvent exchange", Nano Lett., 11:3720-6 (2011).
Van Weemen and Schuurs, "Immunoassay using antigen-enzyme conjugates", FEBS letters, 15:232-6 (1971).
Weissleder, et al., "Ultrasmall superparamagnetic iron oxide: characterization of a new class of contrast agents for MR imaging", Radiology, 175:489-93 (1990).
White and Cuttitta, "bis-(Salicylidene) Ethylenediamine", Analytical Chem., 31:2083-7 (1959).
Xie, et al., "Surface-engineered magnetic nanoparticle platforms for cancer imaging and therapy", Acc. Chem. Res., 44:883-92 (2011).
Yalow and Berson, "Immunoassay of endogenous plasma insulin in man", J Clin Invest., 39:1157-75 (1960).
Zangar, et al., "ELISA microarray technology as a high-throughput system for cancer biomarker validation", Expert Rev. Proteomics, 3:37-44 (2006).

\* cited by examiner

1. Blank
2. Deficient plasma
3~6. Intermediate
7. Normal plasma

NANOCRYSTAL BASED BIOMOLECULE DETECTION

STATEMENT REGARDING FEDERALLY SPONSORED RESEARCH OR DEVELOPMENT

This invention was made with Government Support under Agreement HHSN268201000043C awarded to Gang Bao by the National Heart Lung and Blood Institute of the National Institutes of Health. The Government has certain rights in the invention.

FIELD OF THE INVENTION

The invention is generally related to methods and compositions for detecting target substance using metal/metal oxide nanocrystal.

BACKGROUND OF THE INVENTION

In the past decade, biomolecule detection has become increasingly important in biological studies and clinical applications. In particular, the expressions of lipids, proteins and nucleotides are widely adopted as criteria in disease diagnosis and management, which require sensitive and quantitative determination of the level of these molecular markers (Zangar, R. C. et al., *Expert Rev. Proteomics*, 3:37-44 (2006); Schupbach, J., *AIDS Rev.*, 4:83-92 (2002)). Traditional detection assays relying on small-molecule reporters such as radioisotopes and fluorophores have found little use in these applications because of poor stability, low sensitivity and difficult sample processing. The need for simple and reliable detection methods has led to the development of various inorganic nanoparticle-based probes. With remarkable magnetic, optical or plasmonic properties, these nanoparticles have greatly expanded the scope of specific bioassays (Peng, H. I. and Miller, B. L., *The Analyst*, 136:436-447 (2011); Alivisatos, P., *Nat. Biotechnol.*, 22:47-52 (2004); Dykman, L. and Khlebtsov, N., *Chemical Society Reviews*, 41:2256-2282 (2012)). For instance, quantum dots and gold nanoparticles can drastically increase the sensitivity of immunofluorescence staining, microarrays and microfluidics (Nam, J. M. et al., *Science*, 301:1884-1886 (2003); Nam, J. M. et al., *J. Am. Chem. Soc.*, 126:5932-5933 (2004); Chin, C. D. et al., *Nat Med*, 17:1015-1019 (2011)). Magnetite and maghemite nanoparticles are being utilized for on-site detection of proteins, nucleotides and bacteria (Perez, J. M. et al., *Nat. Biotechnol.* 20:816-820 (2002)), in addition to enriching target molecules in detection assays (Nam, J. M. et al., *Science*, 301:1884-1886 (2003); Lin, P. C. et al., *Small*, 2:485-489 (2006)).

Due to the low intrinsic signal of biomolecules, most existing detection techniques are based on a tagging strategy that links the target molecule to reporters. The number of target molecules is then converted to a specific measure, be it fluorescence signal, radioactivity, or electric current. The ratio between the bound reporters and the target molecules determines the fold of amplification and hence the detection sensitivity of the assay. According to amplification schemes, existing detection techniques can be divided into two categories: direct amplification and enzymatic amplification. In direct amplification, the reporters are conjugated or adsorbed to the surface of detection probes (FIG. 1A). Owing to steric hindrance, the fold of amplification rarely exceeds a few hundreds even with nano- or macro-particle based probes (Nam, 3. M. et al., *Science*, 301:1884-1886 (2003)). Consequently, the techniques employing direct amplification demand ultrasensitive reporters such as radioisotopes, which often rely on specialized instrument for signal acquisition (Nam, 3. M. et al., *Science*, 301:1884-1886 (2003); Nam, J. M. et al., *J. Am. Chem. Soc.*, 126: 5932-5933 (2004); Chin, C. D. et al., *Nat. Med.*, 17:1015-1019 (2011); Perez, J. M. et al., *Nat. Biotechnol.* 20:816-820 (2002); Lin, P. C. et al., *Small*, 2:485-489 (2006); Burtea, C. et al., *J. Inorg. Biochem.*, 99:1135-1144 (2005); Yalow, R. S. and Berson, S. A., The *Journal of clinical investigation*, 39:1157-1175 (1960); Quinn, Z. A. et al., *J. Anal. Atom Spectrom.* 17:892-896 (2002); Merkoci, A. et al., *Analytical Chemistry*, 77:6500-6503 (2005)). In contrast, in enzymatic amplification, the detection probe is linked to an enzyme that can catalyze hydrolysis of chromogenic substrate (FIG. 1B). Enzyme-based amplification has been extensively used in immunosorbent assays and blotting assays for sensitive analyte detection. In particular, enzyme linked immunosorbent assay (ELISA) has been the industrial standard for quantification of protein and other macromolecule since its emergence in 1970s (Engvall, E. and Perlmann, P., *Immunochemistry*, 8:871-874 (1971); Van Weemen, B. K. and Schuurs, A. H. W., *FEBS letters*, 15:232-236 (1971)). However, enzyme-substrate interaction is subjected to a number of variables such as enzymatic activity and incubation conditions. Biomolecule quantification with enzyme-linked probes is hindered by the requirement of stringent control, costly calibration as well as the nonlinear nature of enzymatic catalysis.

Therefore, it is an object of the invention to provide methods and compositions for improved methods for detecting target substances.

SUMMARY OF THE INVENTION

A new signal amplification method exploiting the dense atom packing in metallic nanocrystals has been developed for detecting target substances. (FIG. 1C). Although miniature in size, metallic nanocrystals contain thousands to millions of metal atoms that can be readily extracted through acid dissolution (Table 1). Metal ion-induced chromogenesis has long been employed for photometric determination of trace metals (Sandell, E. B. and Onishi, H., *Photometric Determination of Traces of Metals.* 4th ed., Wiley: New York (1978)). Therefore, by dissolving nanocrystals to individual ions that are stoichiometrically converted to chromophores and quantified photometrically, extremely high signal amplification can be achieved. Signal amplification is fully determined by the total number of atoms in the nanocrystals bound to a single target molecule.

The disclosed nanocrystal amplification method can be implemented with a rich selection of metal/metal oxide nanocrystals and metal-reactive chromogenic substrates. The chromogenic reactions can be either solution-based or surface-based and performed in aqueous or organic phase, supporting a variety of assay formats (Sandell, E. B. and onishi, H., *Photometric Determination of Traces of Metals*. 4th ed., Part 1 (1978)). The data provided herein demonstrate the amplification method by integrating the synthesis and functionalization of wüstite ($Fe_{1-x}O$) nanocrystals and robust ferrous ion-induced chromogenesis in immunosorbent assays and western blot. The nanocrystal amplification method is simple, highly sensitive and more reliable compared to enzymatic amplification. Owing to its superior stability and linearity, the nanocrystal amplification not only facilitates quantification of biomolecule concentration and binding kinetics in laboratory settings, but also empowers instrument-free evaluation of disease markers for on-site diagnostics. This amplification scheme can be applied to nearly all metal/metal oxide nanocrystals, greatly enriching the perspective of current nanoparticle-based bioassays.

One embodiment provides detection agent having a metal/metal oxide nanocrystal conjugated to a binding moiety that specifically binds to a target, wherein the nanocrystals are free of inter-particle magnetic interactions. In a preferred embodiment, the metal/metal oxide is an iron oxide such as wüstite. In other embodiments, the nanocrystal is a copper or cobalt. The nanocrystals can optionally be coated to aid in dispersion in aqueous media, to reduce or inhibit non-specific binding of the nanocrystals, and to provide functional groups for conjugation of binding moieties. Typically, the nanocrystals are coated with polymers such as a combination of 1,2-Distearoyl-sn-glycero-3-phosphoethanolamine-N-[methoxy(polyethylene glycol)-2000] (DSPE-mPEG) and 1,2-distearoyl-sn-glycero-3-phosphoethanolamine-N-[maleimide (polyethylene glycol)-2000] (DSPE-PEG-maleimide).

The binding moiety is typically an antibody or antigen binding fragment thereof. In some embodiments, the binding moiety is an aptamer, lipid, protein, peptide, carbohydrate, or small-molecule ligands.

Another embodiment provides a method for detecting or quantifying a target substance including contacting a sample containing or suspected of containing the target substance with a metal/metal oxide nanocrystal conjugated to a binding moiety that specifically binds to the target substance, inducing the release of the metal ions of the nanocrystals, stoichiometrically converting the metal ions into chromophores; and photometrically detecting or quantifying the chromophores. The chromophores can be photometrically quantified by correlating the photometric data to a predetermined standard curve. For example, photometric quantification can be performed by measuring the absorbance of the sample at the maximum absorption wavelength of the chromophore. When the nanocrystal is wüstite and the chromogenic reagent is ferrozine, the absorbance is measured at 562 nm.

Representative chromophores include, but are not limited to water-soluble chelates of the metal ions with ferrozine molecules or insoluble precipitates of Prussian blue.

Still another embodiment provides a method for detecting or quantifying a target substance by applying a sample containing or suspected of containing a target substance to a solid support comprising a capture reagent immobilized on the solid support, wherein the capture reagent specifically binds the target substance; applying the disclosed detection agent, wherein the detection agent specifically binds the target substance; inducing the release of the metal ions of the nanocrystals, stoichiometrically converting the metal ions into chromophores; and photometrically detecting or quantifying the chromophores A kit containing one or more of the disclosed detection agents and reagents for performing a chromatogenic reaction with by metal ions of the nanocrystal.

BRIEF DESCRIPTION OF THE DRAWINGS

FIG. 1A illustrates "Direct Amplification", whereby reporters (indicated by small spheres) are conjugated or adsorbed directly to the probe surface. The graph (top) illustrates reporter signal is proportional to conjugation ratio. FIG. 1B illustrates "Enzymatic Amplification", whereby the enzyme associated with the detection probe catalyzes hydrolysis of substrate molecules to generate an optical signal. The graph (top) illustrates reporter signal is proportional to enzyme activity. FIG. 1C illustrates "Nanocrystal Amplification", whereby the nanocrystal conjugated with the probe is dissolved by acid into individual metal atoms which are converted to chromophores through a stoichiometric chromogenesis reaction. The graph (top) illustrates reporter signal amplification is proportional to the total number of atoms.

FIG. 4A is a set of Transmission Electron Micrograph (TEM) images showing as-synthesized wüstite nanocrystals (16.5 nm) in toluene (left) and PEGylated and antibody-conjugated IONPs in water (right); scale bar=100 nm. IONPs were negatively stained with methylamine tungstic acid; with negative staining, DSPE-PEG coating and antibody fragments on IONPs are visible as a white shell. FIG. 4B is an image of representative color-developed iron oxide nanoparticle linked immunosorbent assay (ILISA) strips; the left and right three lanes are from the direct ILISA (see FIG. 4C) and competitive ILISA (see FIG. 5C), respectively. FIG. 4C is a dot plot graph showing results of a direct ILISA whereby a 96-well microliter plate was coated with different concentrations of normal mouse IgG and surface bound mouse IgG was detected with a goat anti-mouse IgG polyclonal antibody conjugated to 16.5 nm IONPs. IONP quantity (fmol) is plotted against Normal Mouse IgG quantity (ng/ml). FIG. 4D is a line graph showing the profile of light absorbance in the direct ILISA over time (hr), measured for mouse IgG at 2000 ng/ml (top; ▲), 500 ng/ml (middle; ●) and 0 ng/ml (bottom; ♦), respectively.

FIG. 11A is a dot plot graph of Light Absorbance against quantity of Normal Mouse IgG (ng/ml). Open and closed circles represent detection with 1 and 0.5 μg/ml HRP-antibody, respectively; the mean standard deviation of three measurements is plotted. FIG. 11B is a line graph showing profiles of light absorbance in ELISA plotted against time for mouse IgG at 2000 ng/ml (top; ▲), 500 ng/ml (middle; ●) and 0 ng/ml (bottom; ♦), respectively; for each series, the mean±standard deviation of three measurements is plotted.

FIG. 4B shows the picture of color-developed sample strips corresponding to the data in FIG. 15.

DETAILED DESCRIPTION OF THE INVENTION

I. Definitions

Figure 1A:
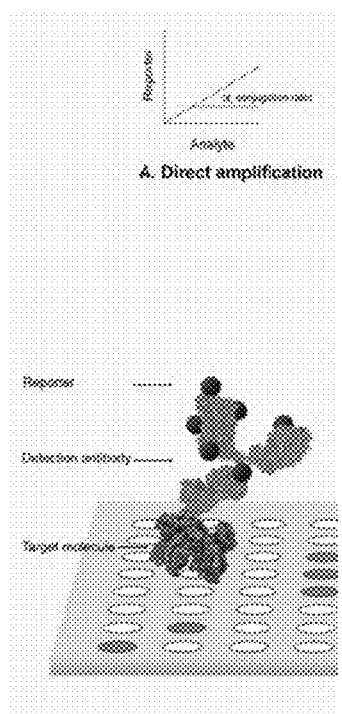
FIGS. 1A-1C show pictorial representations of three different detection assays, whereby the target molecule is detected with probes (e.g. antibodies or antibody fragments) linked to reporters via each of three different amplification schemes, respectively. A graph at the top of each figure illustrates reporter quantity as a function of analyte quantity.
Figure 1B:
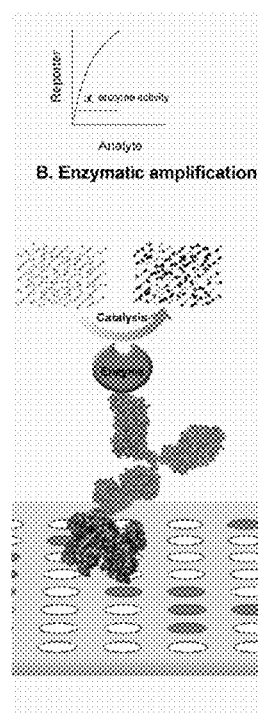
Figure 1C:
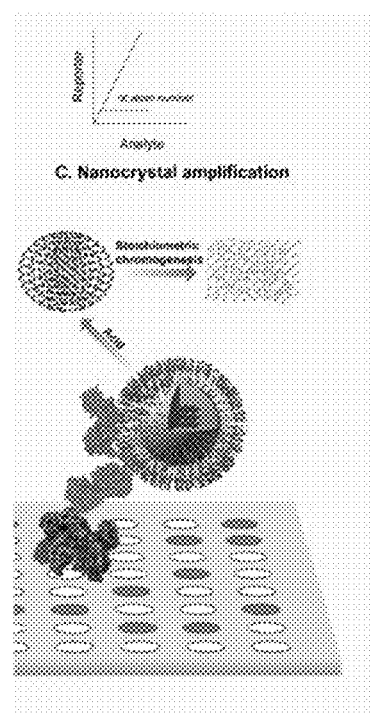

The term "nanocrystal" refers to a crystal that is less than one micrometer in diameter.

The term "ILISA" refers to iron oxide nanoparticle linked immunosorbent assay.

The term "IONP" refers to iron oxide nanoparticles.

The term "ELISA: refers to enzyme-linked immuno sorbent assay.

The terms "targeting moiety," "ligand" or "binding moiety", refer interchangeably to a molecule that binds to a particular target molecule and forms a bound complex. The binding can be highly specific binding, however, in certain embodiments, the binding of an individual ligand to the target molecule can be with relatively low affinity and/or specificity. The ligand and its corresponding target molecule form a specific binding pair. Examples include, but are not limited to small organic molecules, sugars, lectins, nucleic acids, proteins, antibodies and fragments thereof, cytokines, receptor proteins, growth factors, nucleic acid binding proteins and the like which specifically bind desired target molecules, target collections of molecules, target receptors, target cells, and the like.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region thereby converting the $F(ab)'_2$ dimer into a Fab' monomer. The Fab' monomer is essentially a Fab with part of the hinge region. While various antibody fragments are defined in terms of the digestion of an intact antibody, one of skill will appreciate that such Fab' fragments may be synthesized de novo either chemically or by utilizing recombinant DNA methodology. Thus, the term, antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (Huston J. S., et al., *Proc. Nat. Acad. Sci. USA*, 85:5879-5883 (1988)). While the $V_H$ and $V_L$, are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p. The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art. Particularly preferred antibodies should include all that have been displayed on phage (e.g., scFv, Fv, Fab and disulfide linked Fv). Antibody fragments that find use as targeting moieties include without limitation Fab', $F(ab')_2$, Fab, H+L (heavy chain+light chain), single domain antibodies, bivalent minibodies, scFv, bis-scFv, tascFv, bispecific $F(ab')_2$. See, Nelson, et al., *Nature Biotechnology*, 27(4):331-337 (2009) and Holliger, et al., *Nature Biotechnology*, 23(9):1126-1136 (2005).

The term "specifically binds", as used herein, when referring to a targeting moiety or to a biomolecule (e.g., protein, nucleic acid, antibody, etc.), refers to a binding reaction that is determinative of the presence of the target molecule of the targeting moiety or biomolecule in a heterogeneous population of molecules (e.g., proteins and other biologics). Thus, under designated conditions (e.g., binding assay conditions in the case of a targeting moiety), the specified ligand or targeting moiety preferentially binds to its particular "target" molecule and preferentially does not bind in a significant amount to other molecules present in the sample.

The term "metal based or metal induced chromogenic reaction" refers to a chemical reaction between metal ions and a reactant that produces a chromophore.

II. Nanocrystal Amplification

The disclosed signal amplification scheme is based on the number of metal atoms in a nanocrystal, which is very robust and determined by its size once the type of nanocrystal is chosen. This new signal amplification scheme can be applied to most metal/metal oxide nanocrystals using acid dissolution and metal-induced chromogenesis, greatly expanding the arsenal of nanoparticle-based detection methods. The numerous combinations of metal-induced chromogenesis and nanocrystals of various sizes and compositions can lead to a wide range of potential biomedical applications. In particular, since nearly all metal ions can generate chromophores in a stoichiometric manner, it is possible to have multiplexed biomolecule detection by combining orthogonal chromogenesis of different metallic nanocrystals in the same assay.

Two distinctive advantages of the nanocrystal-enabled amplification scheme are exceptional repeatability and instrument-free detection. In many laboratory and clinical applications, samples need to be examined one at a time. In contrast to RIA or ELISA, ILISA eliminates the need of repetitive calibration for each individual experiment. With ILISA, single measurement can be performed and the biomolecule concentration will be calculated with a predetermined universal standard curve, which significantly reduces the cost and the labor required by traditional assays. Further, thanks to the repeatability and tunable dynamic range of ILISA, it allows "instrument-free" detection of many disease markers that vary significantly between healthy and disease states. The IONP-based "instrument-free" detection kits can be a valuable diagnostic tool for on-site medical service or patient screening in developing countries where advanced instruments are not available.

The nanocrystal-based amplification scheme features a very large amplification factor that can be tuned through nanocrystal size and sequential detection, while keeping the linearity preserved. Even without optimization, the detection limit of ILISA reaches low-picomolar level, covering a wide dynamic range of disease markers. The detection sensitivity can be further improved by using large nanocrystals (>30 nm) or even microparticles consisting of clusters of nanocrystals. An alternative approach is to take advantage of fluorogenesis reactions. For example, the detection limit of magnesium with bis-salicylidene-ethylenediamine is 3 orders of magnitude higher than iron-ferrozine chelates, having the potential for ultrasensitive detection (White, C. E. and Cuttitta, F., *Analytical Chemistry*, 31:2083-2087 (1959)). It is also conceivable to incorporate the nanocrystal-based quantification scheme in other bioassay formats such as those using microfluidics and microarrays.

A. Metal/Metal Oxide Nanocrystals

1. Representative Metals and Metal Oxides

Metal-induced chromogenesis exists for nearly all metals. Suitable metal/metal oxide nanoparticle probes can be dissolved with acids. Therefore, suitable nanoparticles includes all metal nanoparticles (except for those formed of inert noble metals such as gold and platinum) and all metal oxide nanoparticles. Metal chromogenesis with distinctive absorption spectra can be combined for multiplex quantification/detection. $Co^{2+}$, $Cu^{2+}$ and $Fe^{2+}$ are representative metals that can be measured simultaneously with ferrozine alone using the distinct absorption peaks of corresponding metal chelates (Kundra, S. K. et al., *Analytical Chemistry*, 46:1605-1606 (1974)). Preferred metal nanocrystals are Co, Cu and Fe nanocrystals. Preferred metal oxide nanocrystal is wüstite, CuO and MgO.

Wüstite has the highest density of Fe atoms. Additionally, wüstite nanocrystals are weakly paramagnetic at all sizes, while maghemite ($\gamma$-$Fe_2O_3$) and magnetite ($Fe_3O_4$) switch from superparamagnetic to ferromagnetic state at 15~20 nm (Hou, Y. L. et al., *Angewandte Chemie-International Edition*, 46, 6329-6332 (2007); Krishnan, K. M. et al., *J. Mater. Sci.*, 41:793-815 (2006); Sun, X. et al., *Nano Lett*, 12:246-251 (2012)). Large wüstite nanocrystals are free of interparticle magnetic interactions, a prerequisite for stable dispersion, and thus a preferred nanocrystal for use in IONP probes.

Preferred nanocrystals have a diameter of 10-50 nm.

2. Coatings

In some embodiments, the nanocrystals are coated with one or more polymers to increase dispersion of the nanocrystals in water and/or to reduce nonspecific binding. The polymer can be a polyethylene glycol or a mixture of polyethylene glycols. In one embodiment, the nanocrystals are coated with 1,2-Distearoyl-sn-glycero-3-phosphoethanolamine-N-[methoxy(polyethylene glycol)-2000] (DSPE-mPEG), 1,2-distearoyl-sn-glycero-3-phosphoethanolamine-N-[maleimide (polyethylene glycol)-2000] (DSPE-PEG-maleimide), or a combination thereof. The polymers can be applied to the nanocrystals using a dual solvent exchange method (Tong, S. et al., *Nano Lett* 2011, 11, 3720-3726 (2011)).

Other common polymers used for iron oxide nanoparticle coating include carbohydrates (such as dextran and starch), proteins (such as albumin), synthetic amphilic polymers (such as biblock or triblock copolymers, for example, poly (maleic anhydride-alt-1-octadecene) and PEG conjugates, poloxamers and poloxamine), synthetic hydrophilic polymers (such as polyamines, dendrimers), and small molecules (such as citric acid, meso-2,3-Dimercaptosuccinic acid, dopamine).

3. Synthesis of Nanocrystals

Metal/metal oxide nanoparticles can be synthesized using conventional techniques. For example wüstite nanocrystals can be synthesized by solvent-free pyrolysis of iron acetylacetonate in oleic acid and oleylamine (Hou, Y. L. et al., *Angewandte Chemie-International Edition*, 46:6329-6332 (2007)). Larger nanocrystals can be obtained by changing the reaction conditions or the precursor compounds (Hou, Y. L. et al., *Angewandte Chemie-International Edition*, 46:6329-6332 (2007); Bronstein, L. M. et al., *Langmuir*, 27:3044-3050 (2011)).

B. Targeting Moiety

The metal/metal oxide nanocrystals can be conjugated to a targeting moiety that specifically binds to a target substance to be detected or quantified. Preferred targeting moieties include, but are not limited to an antibody or antigen-binding fragment thereof, a unibody, an affybody, an aptamer, peptide, carbohydrate, polymer, a ligand, and a polynucleotide. In some embodiments, the targeting moiety is an antibody or antibody fragment. In some embodiments, the targeting moiety is an antibody fragment selected from the group consisting of scFv, an Fv, an Fab, an Fab', an F(ab')$_2$, a bis-scFv, heavy-light chains. In some embodiments, the targeting moiety is a monoclonal antibody. In some embodiments, the targeting moiety is a polyclonal antibody. In some embodiments, the antibody is a single domain antibody, a nanobody, a minibody, a diabody, a triabody, or a tetrabody. In some embodiments, the antibody is an IgG.

In various embodiments, the targeting moieties can be the same or different; the targeting moieties can specifically or preferentially bind to the same or different target antigens or biomarkers. In some embodiments, the targeting moieties are all the same. In some embodiments, the targeting moieties are attached to a scaffold having a plurality of different targeting moieties. In some embodiments, the targeting moieties are attached to a scaffold have at least two different targeting moieties that bind different targets/epitopes on a target.

In some embodiments, the targeting moiety specifically or preferentially binds to a cell or epitope on a cell from a cancer selected from the group consisting of breast cancer, colorectal cancer, NSCLC, lung cancer, bone cancer, pancreatic cancer, skin cancer, cancer of the head or neck, cutaneous melanoma, intraocular melanoma, uterine cancer, ovarian cancer, rectal cancer, anal region cancer, stomach cancer, gastric cancer, colon cancer, breast cancer, uterine cancer, fallopian tube carcinoma, endometrial carcinoma, cervical carcinoma, vaginal carcinoma, vulval carcinoma, Hodgkin's Disease, esophagus cancer, small intestine cancer, endocrine system cancer, thyroid gland cancer, parathyroid gland cancer, adrenal gland cancer, soft tissue sarcoma, urethral cancer, penis cancer, prostate cancer, bladder cancer, kidney cancer, ureter cancer, renal cell carcinoma, renal pelvis carcinoma, mesothelioma, hepatocellular cancer, biliary cancer, chronic leukemia, acute leukemia, lymphocytic lymphoma, CNS neoplasm, spinal axis cancer, brain stem glioma, glioblastoma multiform, astrocytoma, schwannoma, ependymoma, medulloblastoma, meningioma, squamous cell carcinoma and pituitary adenoma tumors, and tumor metastasis. In some embodiments, the targeting moiety specifically or preferentially binds to Her2/neu.

The targeting moiety can specifically bind viral proteins or viral epitopes, for example Human Immunodeficiency Virus proteins or epitopes, hepatitis virus proteins or epitopes, papilloma virus proteins or epitopes, bacterial proteins or epitopes, steroids, hormones, opiates, tetrahydrocannabinol, and alkaloids such as cocaine.

The targeting moiety can specifically bind disease markers in blood samples. Such disease markers include markers of inflammatory diseases, cancer, infectious diseases and cardiovascular diseases, for example, all classes of immunoglobulin, complementary factors, interleukins, proteases (such as MMPs, elastase and cathepsins), integrins, C-reactive protein, fibronectin, thrombin, insulin, proteins associated with virus or bacterium infection, and cancer associated growth factors (such as VEGF, bFGF etc.), as well as fragments of DNA and RNA in plasma.

The targeting moiety can specifically bind disease markers in urine samples, including proteins associated with urinary infections and cancer markers associated with kidney cancer and prostate cancer.

In some embodiments, the targeting moiety specifically or preferentially binds to a primary antibody, and the primary antibody specifically binds to a target of interest.

The targeting moiety can specifically or preferentially bind to the Fc portion of an immunoglobulin (e.g., is a secondary antibody). For example, the targeting moiety may specifically or preferentially bind to the Fc portion of an IgG, an IgA, an IgD or IgM antibody.

C. Linking the Nanocrystals and Targeting Moieties

The targeting moiety can be linked directly to the nanocrystals or through a spacer group. Spacer groups include alkyl alkylaryl or alkylheteroaryl spacer groups having a chain length from about C1 to about C12, or a subrange thereof such as C1 to C3, C2 to C4 etc. The spacer group is optionally substituted by one or more double and/or triple bonds. In certain aspects the total number of atoms in the alkylaryl and alkylheteroaryl groups is from about 6 to about 50.

The nanocrystals can be conjugated to the targeting moiety using conventional conjugation chemistry. Crosslinking is the process of chemically joining two or more molecules by a covalent bond. The technique, often called bioconjugation when referring to its use with proteins and other biomolecules.

Crosslinking reagents (or crosslinkers) are molecules that contain two or more reactive ends capable or chemically attaching to specific functional groups (primary amines, sulfhydryls, etc.) on proteins or other molecules. The cross-linking chemistry can be any one of the following: Carboxyl-to-amine using for example Carbodiimides (EDC); Amine-reactive using NHS Esters and Imidoesters; Sulfhydryl-reactive using Maleimides, Haloacetyls and Pyridyldisulfides; Carbonyl-reactive using Hydrazides and Alkoxyamines or Photoreactive using Aryl Azides and Diazirines.

In a preferred embodiment, the metal/metal oxide nanocrystals are coated with a polymer containing a functional group that enables the nanocrystal to be crosslinked to the targeting moiety. For example, the nanocrystals can be coated with a polymer containing maleimide groups. The maleimide groups can be directly conjugated with thiolated antibody fragments, which can be obtained by antibody reduction with 2-mercaptoethylamine.

The targeting moiety can also be linked to nanocrystals through disulfide bond, nucleotide binding, hydrophobic interactions (for example, and biotin-avidin binding. Small molecule binding moieties can be conjugated to a binding moiety using general synthetic chemistry. The binding moiety can then be linked to nanocrystals using chemistries mentioned above.

D. Substrates

The disclosed detection agents can be attached to a solid support or substrate. The solid support can be a microtiter plate, a dipstick, nitrocellulose, beads, and culture dish. The solid support can be planar. Typically the solid support is made of plastic.

E. Nanocrystal Amplification Methods

The disclosed detection agents can be used in many detection methods similar to ELISA detection methods. The chromogenic reactions can be either solution-based or surface-based and performed in aqueous or organic phase, supporting a variety of assay formats (Sandell, E. B. and Onishi, H., *Photometric Determination of Traces of Metals*, 4$^{th}$ ed; Wiley: New York (1978); which is incorporated by reference in its entirety). The following detection assays are exemplified using antibodies; however, it will be appreciated that the targeting moiety can be any of the targeting moieties discussed above.

1. Direct and Indirect Detection Assays

The steps of the detection assay includes adding a sample, typically a buffered solution containing or suspected of containing the target substance to be tested for to each well of a microtiter plate, where it is given time to adhere to the plate. A blocking solution of nonreacting protein, such as bovine serum albumin or casein, is typically added to coat any plastic surface in the well that remains uncoated to reduce nonspecific binding.

A primary antibody specific for the target substance is added to the micro titer plate. The primary antibody could also be in the serum of a donor to be tested for reactivity towards the target substance. Direct detection occurs if the primary antibody is conjugated to the disclosed nanocrystals.

In indirect detection assays, the disclosed detection agent, typically an antibody conjugated to a nanocrystal as described above, is added, which will bind the primary antibody.

It will be appreciated that the microtiter plates can be washed one or more times between steps to remove excess reagents.

To produce photometrically detectable chromophores from the detection agent, the nanocrystals are dissolved into individual ions that are stoichiometrically converted to chromophores. Metal-based chromogenic reactions are known in the art (See, Sandell, E. B. and Onishi, H., *Photometric Determination of Traces of Metals*, 4$^{th}$ ed; Wiley: New York (1978); which is incorporated by reference in its entirety). A representative method for dissolving the nanocrystals is acid dissolution. The chromophores are then photometrically detected or quantified. Microtiter plate reader is typically used for photometric detection or quantification.

When the metal/metal oxide nanocrystals are from Fe, the metal ions can be measured by combining acid dissolution, reduction and ferrozine chelation. $Fe^{2+}$ can also stoichiometrically react with potassium ferricyanide, resulting in either dispersed colloid or insoluble precipitates of Prussian blue (FIG. 2B)

The disclosed methods may be run in a qualitative or quantitative format. Qualitative results provide a simple positive or negative result (yes or no) for a sample. In quantitative assays, the optical density (OD) of the sample is compared to a standard curve, which is typically a serial dilution of a known-concentration solution of the target molecule. The standard curve can be predetermined and is not necessarily performed for each assay. For example, if a test sample returns an OD of 1.0, the point on the standard curve that gave OD=1.0 must be of the same analyte concentration as the sample.

An important application of the indirect detection assay is to measure the binding affinity/dissociation constants of immunoglobulins and their target antigens or ligand/receptor pairs. The binding affinity can be calculated by fitting the optical density with the following equation, $$NP = \frac{NP_{max} \times C_A}{K_d + C_A} \quad (1)$$

where $NP_{max}$ is the saturation level of NP, $C_A$ is the concentration of the mouse antibody in solution and $K_d$ is the dissociation constant between the mouse antibody and its antigen.

2. Competitive Detection Assays

A representative competitive detection assay includes the steps of: incubating a sample containing or suspected of containing the target substance with an unlabeled antibody specific for the target substance to produce antibody/target substance complexes; the complexes are then added to a well in a microtiter plate coated with the target substance; the plate is optionally washed, so unbound antibody is removed; adding the disclosed detection agent specific to the primary antibody, releasing the metal ions from the nanocrystal; performing a metal-based chromogenic reaction to produce chromophores from the metal ions; and photometrically detecting or quantifying the chromophores.

3. Sandwich Assays

The disclosed detection agents can also be used in sandwich assays. A representative sandwich assay includes the steps of preparing surface, for example a microtiter plate, with a known quantity of a capture antibody is immobilized; optionally blocking nonspecific binding sites on the surface; adding a sample containing or suspected of containing a target substance to the plate; optionally washing the plate to remove excess reagents; adding a specific antibody that binds to target substance; adding the disclosed detection agents that bind specifically to the antibody's Fe region (nonspecific); optionally washing the plate to remove excess reagents; releasing the metal ions from the nanocrystal; performing a metal-based chromogenic reaction to produce chromophores from the metal ions; and photometrically detecting or quantifying the chromophores.

4. Western Blots

Conventional western blot assays can be modified to use the disclosed detection agents. After the target protein is transferred to a substrate such as a cellulose membrane, a detection agent specific for the target protein is incubated with the membrane. The protein bands are visualized using a metal-based chromogenic reaction to form chromophores from the metal ions released from the nanocrystals. For example, when Fe nanocrystals are used, the membrane can be incubated in HCL and potassium ferrocyanide.

5. Tunable Signal Amplification

Figure 6A:
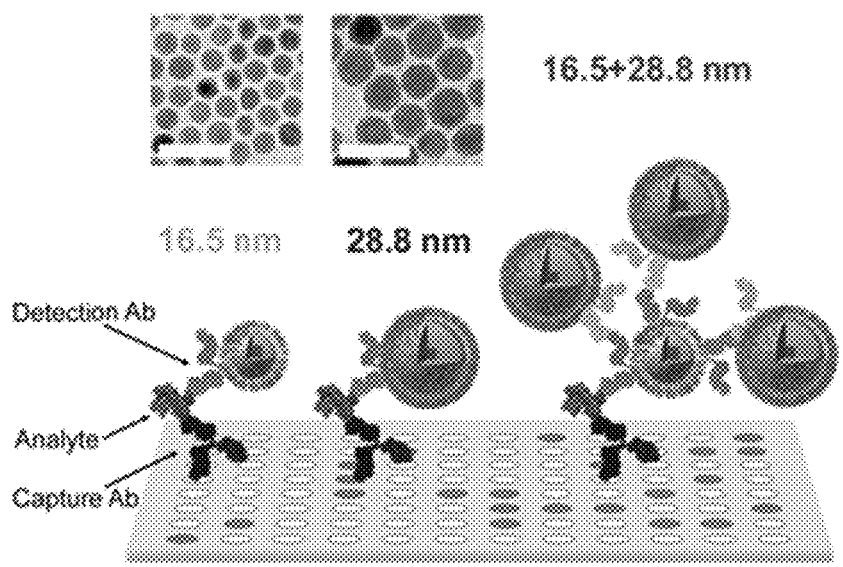
FIG. 6A is a schematic diagram of signal amplification employed in (FIG. 6B) for enhanced detection sensitivity in sandwich ILISA. Insets are TEM images of 16.5 nm (left panel) and 28.8 nm (right panel) wüstite nanocrystals, respectively; scale bar=50 nm.
Figure 6B:
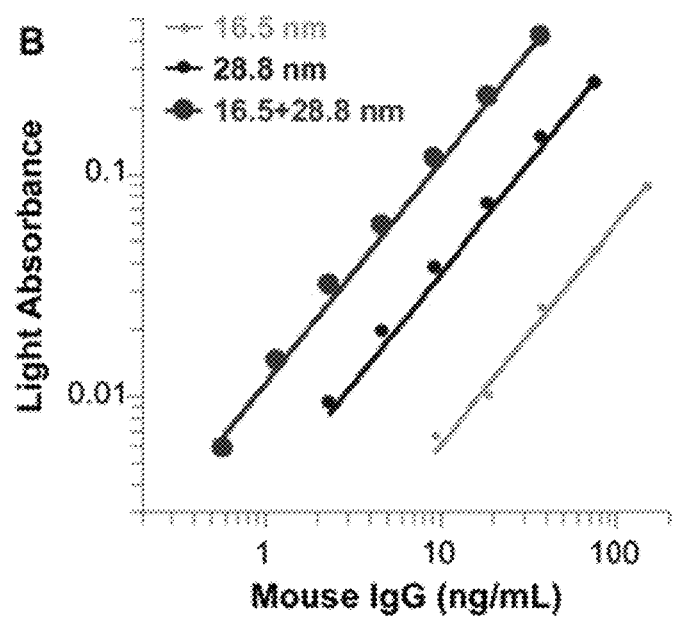
FIG. 6B is a dot plot graph showing Light Absorbance (Log 10) plotted against the quantity of Mouse IgG (Log 10 ng/mL), detected with goat antibody linked to 16.5 nm IONPs (small dots), 28.8 nm IONPs (medium dots) or 16.5 nm IONPs but subsequently amplified using secondary IONPs (28.8 nm IONPs conjugated with a rabbit antibody raised against goat IgG; large dots), respectively. For each set of data, the mean of three measurements and fitted lines are plotted. The same data plotted with error bars in linear scale is provided in FIG. 13
Figure 13:
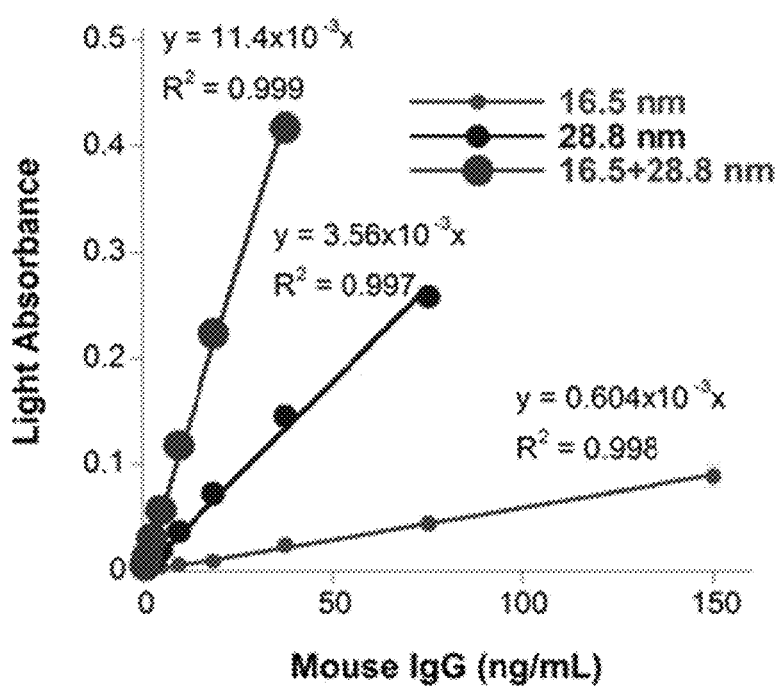
FIG. 13 is a dot plot graph showing the signal amplification in sandwich ILISA. Linear values for Light Absorbance are plotted against linear values for the quantity of Mouse IgG (ng/mL), detected with goat antibody linked to 16.5 nm IONPs (small dots), 28.8 nm IONPs (medium dots) or 16.5 nm IONPs but amplified using secondary IONPs (28.8 nm IONPs conjugated with a rabbit antibody raised against goat IgG; large dots), respectively. Mean±standard deviation of three measurements are plotted. The detection sensitivity of the three assays can be evaluated by the slope of fitted lines.

Signal amplification of the disclosed detection methods can be optimized by varying the size and number of nanocrystals bound to an individual analyte molecule. By increasing the core size of the nanocrystals from 16.5 to 28.8 nm (d=28.8±4.4 nm), the signal intensity of a sandwich ILISA was increased by 5.89 folds, consistent with the volume ratio between the two nanocrystals (FIG. 6B and FIG. 13). As in traditional immunosorbent assays, the detection sensitivity of ILISA can be further enhanced by amplification with secondary detection agents. As illustrated in FIG. 6A, the analyte was initially detected by goat antibody conjugated 16.5 nm detection agents, which were in turn bound by secondary probes of 28.8 nm detection agents conjugated with a rabbit anti-goat IgG antibody. With this two-step approach, the amplification was increased by 18.84 fold compared with using 16.5 nm probes alone and mouse IgG was detected at 0.59 ng/mL or 3.9 pM. Interestingly, the fold increase in amplification can be attributed as having one 16.5 nm probe bounded by three 28.8 nm probes per analyte (1+3×5.89=18.67 vs. 18.84).

F. Kits

Kits are also provided. The kits can include one or more of the disclosed detection agents as well as reagents for a metal based chromogenic reaction. The kit optionally includes a solid substrate such as a microtiter plate or a culture dish. Typically the components of the kit are packaged in a container.

Alternatively, the kit can contain reagents for producing one or more of the disclosed detection agents.

EXAMPLES

Example 1: Wüstite Nanocrystal-Based Detection Scheme

Materials and Methods

Iron (III) acetylacetonate (99.9%), oleic acid (90%), oleylamine (70%), toluene (99.9%), chloroform (99%), DMSO (99.9%), hydrochloric acid, hydroxylamine HCl, sodium hydroxide, ammonium acetate, ferrozine, potassium ferrocyanide, iodoacetamide and lipopolysaccharide (LPS) were purchased from Sigma-Aldrich. 1,2-Distearoyl-sn-glycero-3-phosphoethanolamine-N-[methoxy(polyethylene glycol)-2000] (DSPE-mPEG) and 1,2-distearoyl-sn-glycero-3-phosphoethanolamine-N-[maleimide (polyethylene glycol)-2000] (DSPE-PEG-maleimide) were purchased from Avanti Polar Lipids. 2-Mercaptoethylamine-HCl (MEA) was purchased from Thermo Scientific. All chemicals were used without modification. Normal mouse IgG and ABTS kit were purchased from. Vector Laboratories. Normal human IgG, goat anti-mouse IgG polyclonal antibody and rabbit anti-goat IgG polyclonal antibody, mouse anti-human VCAM-1 monoclonal antibody, goat anti-human VCAM-1 polyclonal antibody and recombinant human VCAM-1 were purchased from R&D systems. Rabbit anti-mouse IgG polyclonal antibody, mouse anti-human IgG monoclonal antibody, rabbit anti-human factor X polyclonal antibody and human factor X were purchased from Abcam. Horseradish peroxidase conjugated goat anti-mouse IgG polyclonal antibody was purchased from Santa Cruz Biotechnology. Human factor X deficient plasma was purchased from Haematologic Technologies. HUVEC was purchased from Life Technologies and cultured according to vendor's instructions.

96-well ELISA plates were purchased from R&D systems. Vivaspin 20 centrifugal filter tubes (MW=100 k) were purchased from VWR International. Amicon centrifugal filter tubes (MW=10 k) were purchased from EMD Millipore.

Estimation of the Number of Fe Atoms Per Wüstite Nanocrystal

Assuming a uniform fcc structure, a consistent molecular formula of FeO and a perfect spherical shape of wüstite nanocrystals, the number of Fe atoms in each nanocrystal can be calculated with the following equation.

$$N = \rho N_A \frac{\pi D^3}{6M} \quad (2)$$

Where $\rho$ is the density of bulk wüstite (5.7 g/cm$^3$), $N_A$ is the Avogadro constant, D is the diameter of nanocrystals, and M is the molecular weight of wüstite (72 Dalton). Wüstite has a nonstoichiometric formula of $Fe_{1-x}O$ (1−x=0.83-0.96). But assuming a formula of FeO only leads to less than 5% overestimation of the atom number. The surface of wüstite nanocrystals can be slowly oxidized to other iron oxide upon long exposure to air. But this will not change the Fe atom number per nanocrystal. The average diameter of the wüstite nanocrystals used in this study was measured from TEM images of freshly synthesized nanocrystals with an automated program in ImagePro Plus® software. At least 500 particles were counted for each type of nanocrystals.

Results

Iron oxide nanoparticles (IONP) have received extensive research interests for applications in recording media, solid state batteries, chemical catalysts, detection assays, magnetic resonance imaging and drug/gene delivery (Perez, J. M. et al., *Nat. Biotechnol.*, 20:816-820 (2002); Lin, P. C. et al., *Small*, 2:485-489 (2006); Burtea, C. et al., *J. Inorg. Biochem.*, 99:1135-1144 (2005); Gao, L. et al., *Nat. Nanotechnol.*, 2:577-583 (2007); Poizot, P. et al., *Nature*, 407: 496-499 (2000); Xie, J. et al., *Acc. Chem. Res.*, 44:883-892 (2011)). IONPs were chosen as the detection probes to take advantage of the well-developed synthesis method for convenient size control (Kolesnichenko, V. L. et al., *Chem. Mater.*, 16:5527-5534 (2004); Weissleder, R. et al., *Radiology*, 175:489-493 (1990); Sun, S. et al., *J. Am. Chem. Soc.*, 126:273-279 (2004); Jana, N. R. et al., *Chem. Mater.*, 16:3931-3935 (2004); Jun, Y. W. et al., *Journal of the American Chemical Society*, 127:5732-5733 (2005); Hou, Y. L. et al., *Angewandte Chemie-International Edition*, 46:6329-6332 (2007); Hyeon, T. et al., *Nature Materials*, 3:891-895 (2004); Bronstein, L. M. et al., *Langmuir*, 27:3044-3050 (2011)). It is also noteworthy that Fe element only presents at low abundance in a few proteins such as ferritin, hemoglobin, transferrin and cytochromes, etc. in most biological specimens. Among all six known forms of iron oxides, wüstite has the highest density of Fe atoms. Additionally, wüstite nanocrystals are weakly paramagnetic at all sizes, while maghemite ($\gamma$-$Fe_2O_3$) and magnetite ($Fe_3O_4$) switch from superparamagnetic to ferromagnetic state at 15~20 nm (Hou, Y. L. et al., *Angewandte Chemie-International Edition*, 46:6329-6332 (2007); Krishnan, K. M. et al., *J. Mater. Sci.*, 41:793-815 (2006); Sun, X. et al., *Nano. Lett.*, 12:246-251 (2012)). Large wüstite nanocrystals are free of inter-particle magnetic interactions, a prerequisite for stable dispersion, and thus used in IONP probes.

Fe atoms in IONPs can be extracted and converted to individual ferrous ions ($Fe^{2+}$) by sequential treatments with acids and reducing agents. Among more than a dozen of $Fe^{2+}$-based chromogenic reactions, $Fe^{2+}$ can form optically stable and water-soluble chelates with ferrozine molecules, the solution of which changes from transparent to sharp purple in appearance upon chelation ($\epsilon_{562\ nm}$=2.79×$10^4$ $M^{-1}$ $cm^{-1}$) (FIG. 2A) (Sandell, E. B. and Onishi, H., *Photometric Determination of Traces of Metals*, 4$^{th}$ ed; Wiley: New York (1978); Stookey, L. L., *Analytical Chemistry*, 42:779-781 (1970)). In solution-based immunosorbent assays, IONPs can be measured by combining acid dissolution, reduction and ferrozine chelation. $Fe^{2+}$ can also stoichiometrically react with potassium ferricyanide, resulting in either dispersed colloid or insoluble precipitates of Prussian blue (FIG. 2B). The latter is useful for detecting IONPs in immunohistochemistry or blotting assays, which require semi-quantification and localization of target molecules on a surface.

Figure 3:
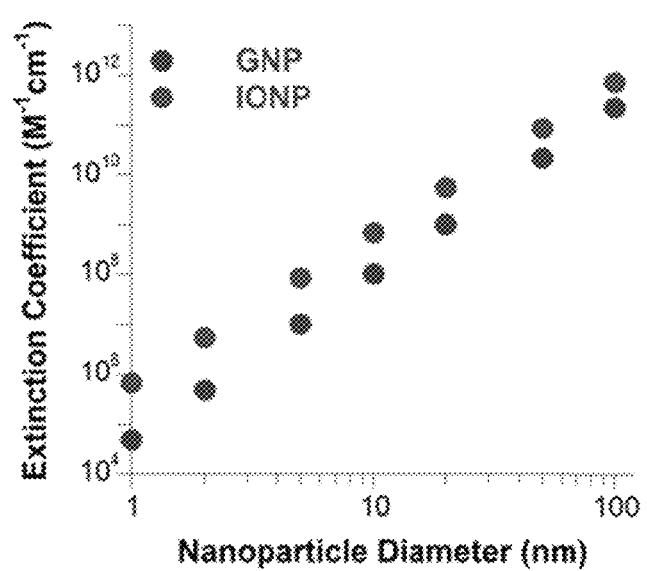
FIG. 3 is a dot plot graph of the Extinction coefficient (Log 10 $M^{-1}$ $cm^{-1}$) of wüstite nanocrystals (IONP; top series) and gold nanoparticles (GNP; bottom series), respectively, over Nanoparticle Diameter (Log 10 nm). The extinction coefficients of wüstite nanospheres are estimated based on ferrozine chelation, and those of gold nanospheres are calculated with a published equation, respectively.

Using the nanocrystal amplification scheme, IONPs can achieve exceptional detection sensitivity. For example, there are 112,039 Fe atoms in a 16.5 nm wüstite nanocrystal. With the ferrozine method, the equivalent molar extinction coefficient of 16.5 nm wüstite nanocrystals, which is defined as the total light extinction of derived iron-ferrozine chelates, is 3.07×$10^9$ $M^{-1}$ $cm^{-1}$. To our knowledge, this is among the highest of all nanoparticles of similar size. Indeed, the equivalent molar extinction of wüstite nanocrystals is consistently higher than the molar extinction of gold nanospheres within the range of 1 to 100 nm (FIG. 3). IONPs can be reliably measured at femtomole to attomole quantities in a 96-well microtiter plate, a standard format of immunosorbent assays (Table 1).

TABLE 1

Wüstite nanocrystals - atom counts and detection sensitivity.

| | Diameter (nm) | | | | |
|---|---|---|---|---|---|
| | 5 | 10 | 20 | 50 | 100 |
| Number of iron atoms[a] | 3,118 | 24,941 | 199,530 | 3,117,649 | 24,941,194 |
| Detection limits[b] | 32 fmol | 4 fmol | 501 amol | 32 amol | 4 amol |

Figure 2A:
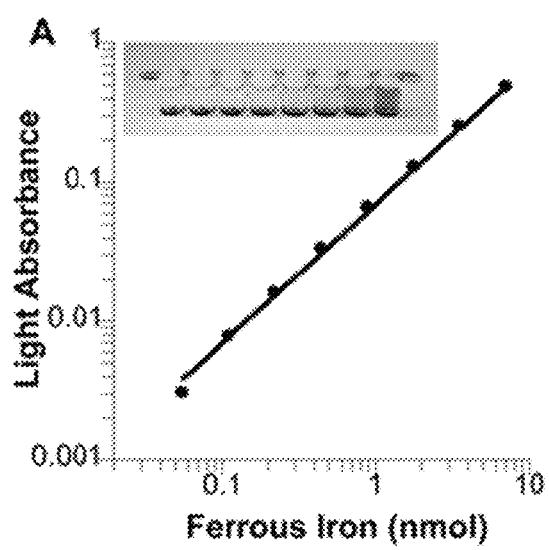
FIG. 2A is a dot plot graph showing Light absorbance (Log 10 at 562 nm) over the quantity of Ferrous Iron (Log 10 nmol); the mean of three measurements and a fitted line are plotted. Inset (top) is an image of eight wells from a 96-well microtiter plate, corresponding to the eight data points in the graph, showing that $Fe^{2+}$ chelation by ferrozine generates a sharp purple color.
Figure 2B:
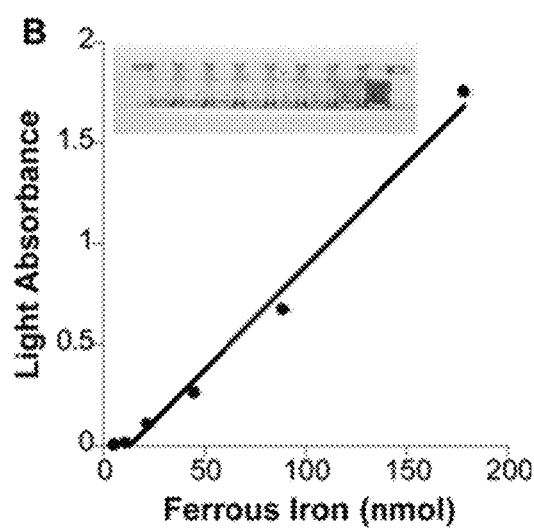
FIG. 2B is a dot plot graph of the Prussian blue reaction, showing Light Absorbance at 790 am, measured immediately after reaction over quantity of Ferrous lion (nmol); the mean of three measurements and error bars, showing standard deviations, and a fitted line are plotted. Inset (top) is an image of eight wells from a 96-well microtiter plate, corresponding to the eight data points in the graph, showing that the product of $Fe^{2+}$ coordinated with potassium ferricyanide is a bright blue colloid.

[a]The number of Fe atoms per nanocrystal was estimated as shown above.
[b]The detection limits of wustite nanocrystals are calculated for ferrozine assay performed in 96-well plates with the detection limit of ferrous ions equal to 0.1 nmol (FIG. 2A).

Example 2: Synthesis of Wüstite Nanocrystals 16.5 nm wüstite nanocrystals were synthesized using a modified protocol according to a previous publication (Hou, Y. L. et al., *Angewandte Chemie-International Edition*, 46:6329-6332 (2007)). Larger nanocrystals can be obtained using similar procedures (Hou, Y. L. et al., *Angewandte Chemie-International Edition*, 46:6329-6332 (2007); Bronstein, L. M. et al., *Langmuir*, 27:3044-3050 (2011)). First, 12 mmol Fe(acac)$_3$, 75 mmol oleic acid and 105 mmol oleylamine were added to a 250 mL three-neck round bottom flask. The solution was mixed vigorously with a magnetic stir bar throughout the reaction. The reaction included three steps. First, the solution was incubated at 120° C. under partial vacuum for 2 hours. After that, the flask was heated to 220° C. with a ramp rate of 5° C./min and incubated at this temperature for 30 minutes under a flow of argon. Finally, the solution was heated to 300° C. with a ramp rate of 2° C./min and incubated at this temperature for 30 minutes under argon. After the reaction, the heating mantle was removed and the solution was cooled to room temperature.

To collect synthesized wüstite nanocrystals, 100 mL absolute ethanol was added to the solution. The solution was centrifuged at 5,000 g, room temperature for 10 minutes and the supernatant was discarded. The black pellets could be easily dispersed with toluene. To remove free oleic acid and oleylamine in the solution, the nanocrystals were washed by ethanol precipitation two more times. After the last wash, the pellets were dried with a beam of argon gas and dispersed with toluene. To remove smaller nanocrystals, the toluene solution was mixed with ethanol at a ratio of 2:1 (vol:vol). The solution was centrifuged at 5,000 g, room temperature for 10 minutes and the pellets were collected. During this procedure, large nanocrystals precipitated preferentially due to higher surface energy.

Example 3: Surface Coating and Maleimide Activation of Wüstite Nanocrystals

Figure 9:
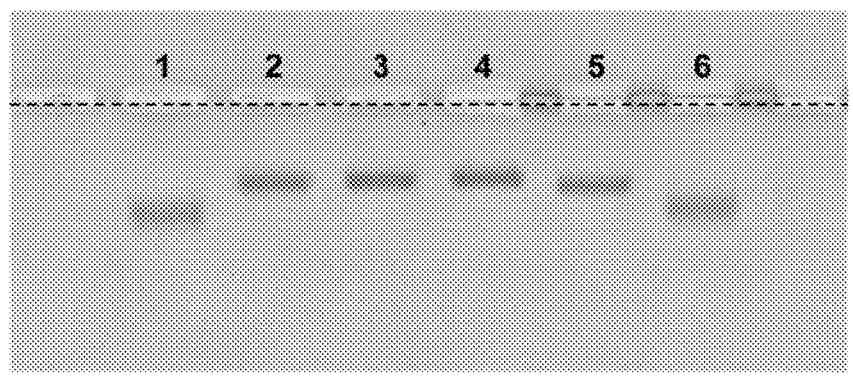
FIG. 9 is an image of an agarose gel containing maleimide activated IONPs, showing lanes 1-6. Lanes 1 and 6 contain IONPs with maleimide hydrolyzed in PBS. Lanes 2-5 contain IONPs incubated in cold deionized water for 90 minutes (lane 2), 5 hours (lane 3), 24 hours (lane 4) and 48 hours (lane 5), followed by MEA reaction, respectively. The wells are marked by a dashed line.

Water-dispersible and maleimide-functionalized iron oxide nanoparticles were synthesized by coating wüstite nanocrystals with amphiphilic DSPE-PEG copolymers using a dual solvent exchange method (Tong, S. et al., *Nano Lett.*, 11:3720-3726 (2011)). In a typical coating procedure, 0.4 mL of the nanocrystals (5 mg Fe/mL in toluene), 0.6 mL of DSPE-mPEG (10 mg/mL in chloroform), 0.09 mL of DSPE-PEG-maleimide (2 mg/mL in chloroform) and 1 mL of chloroform were mixed in a 250 mL flask. 8 mL of DMSO was added to the flask drop-wise with gentle shaking over a period of 20 minutes. Then the flask was connected to a vacuum pump to remove toluene and chloroform from the mixture. The evaporation was stopped when the solution weighed 7.04 g. After that, 30 mL of distilled water was slowly added to the DMSO solution and DMSO was removed by solvent exchange with Vivaspin centrifugal filter tubes (MW=100 k). To remove empty micelles formed by DSPE-mPEG and DSPE-PEG-maleimide, the solution was centrifuged twice (50,000 g, 4° C. and 1 hour). At the end of centrifugation, the pellet was dispersed with distilled water. For 16.5 nm wüstite nanocrystals, the resulting IONPs had an average hydrodynamic diameter of 39 nm as measured with dynamic light scattering (DynaPro Nanostar, Wyatt Technology). Gel electrophoresis shows that the IONPs had a highly uniform size distribution and maleimide density (FIG. 9). In addition, maleimide is available for antibody conjugation for at least 24 hours if IONPs are dispersed in distilled water at 4° C.

Example 4: Conjugation of Antibodies to IONPs

The antibodies were reduced with 2-mercaptoethylamine-HCl (MEA). Reduced antibody fragments with free sulfhydryl groups were conjugated to maleimide activated IONPs through thiol-maleimide reaction. In a typical reaction, 100 μg antibody was mixed with MEA in 200 μL PBS-EDTA (100 mM phosphate, 10 mM EDTA and pH 7.2) and incubated at 37° C. for 2 hours. The concentrations of MEA were 30 mM for rabbit antibodies and 100 mM for goat and sheep antibodies. Reduced antibody fragments were washed five times with sodium acetate (100 mM, pH 5.5) in Amicon centrifugal filter tubes (MW=10K). After washes, IgG concentration was determined by light absorption at 280 nm ($A_{280\ nm}$=1.36 for 1 mg/mL IgG). The IONPs were mixed with reduced IgG at 1:3 molar ratio (e.g. 72 μg antibody fragments for each 1000 μg Fe of 16.5 nm IONPs) in PBS. The antibody concentration in the reaction mixture was fixed at 100 nM. The solution was incubated at room temperature overnight. After conjugation, the solution was centrifuged twice (50,000 g, 4° C. and 1 hour) and supernatant with unconjugated antibody fragments was discarded.

Example 5: Protein Coating of 96-Well Microtiter Plates

In ILISA or ELISA, the plates were prepared in two steps. First, purified capture antibodies or antigens were adsorbed to the plate surface. Then the plate surface was saturated with BSA to prevent nonspecific interactions between the plate surface and other protein molecules. For example, to prepare the plate for the direct immunosorbent assay, 100 μL of normal mouse IgG at designated concentrations was added to each well. The plate was covered with a sealer and incubated at 4° C. for 24 hours. After incubation, the plate was washed three times with PBS containing 0.05% Tween-20. Each well was filled with 300 μL of 1% BSA in PBS. After incubated at 4° C. for another 24 hours, the plate was ready to use. The plates used in other ILISAs were prepared similarly (Table 2).

Example 6: Detecting Surface-Bound Proteins with IONPs in 96-Well Plates

Antigen bound 96-well plates were prepared according to the standard ELISA protocol (Table 2). In a typical ILISA, 16.5 nm IONP-based probes were diluted with PBS containing 1% BSA to a final concentration of 100 μg Fe/mL. 100 μL of IONP solution was added to each well. The plate was cover with a plate sealer and incubated at 37° C. for 1 hour with vigorous shaking. After incubation, the plate was decanted and washed with PBS containing 0.05% Tween-20®. To measure Fe atoms of bound IONPs, the wells were incubated with 50 μl of 6 M HCl at room temperature for 15 minutes. Then 70 μl of 4 M NaOH and 80 μl of color development solution were sequentially added to each well. The color development solution was made by mixing 1.5 mL 7.5 M ammonium acetate, 2.5 mL 5% hydroxylamine hydrochloride solution and 4 mL 0.1% ferrozine solution immediately before use. After mixing with pipettes, the light absorbance of the solutions was measured at 562 nm with 810 nm as the reference using a microplate reader.

Example 7: Application of IONPs in Western Blot

Mouse IgG at designated quantities and BSA were analyzed with gel electrophoresis in Nuge 4-12% Bis-Tris gel. After the protein bands were transferred onto a cellulose membrane, mouse IgG was detected with 16.5 nm IONPs conjugated with a rabbit anti-mouse IgG polyclonal antibody. In brief, the membrane was blocked with non-fat milk at room temperature for 60 minutes. Then the membrane was incubated with the IONP solution (100 μg/mL in PBS with 1% BSA) at room temperature for 60 minutes. After washes, the membrane was immersed in a solution containing 2% potassium ferrocyanide and 2 M HCl, and sharp blue bands appeared after 5 minute incubation. The membrane was imaged with an office scanner.

Example 8: Tunable Signal Amplification of IONP-Based Detection

Signal amplification of ILISA can be further optimized by varying the size and number of nanocrystals bound to an individual analyte molecule. By increasing the core size of IONPs from 16.5 to 28.8 nm (d=28.8±4.4 nm), the signal intensity of a sandwich ILISA was increased by 5.89 folds, consistent with the volume ratio between the two nanocrystals (FIG. 6B and FIG. 13). As in traditional immunosorbent assays, the detection sensitivity of ILISA can be further enhanced by amplification with secondary IONPs. As illustrated in FIG. 6A, the analyte was initially detected by goat antibody conjugated 16.5 nm IONPs, which were in turn bound by secondary probes of 28.8 nm IONPs conjugated with a rabbit anti-goat IgG antibody. With this two-step approach, the amplification was increased by 18.84 fold compared with using 16.5 nm probes alone and mouse IgG was detected at 0.59 ng/mL or 3.9 pM. Interestingly, the fold increase in amplification can be attributed as having one 16.5 nm probe bounded by three 28.8 nm probes per analyte (1+3×5.89=18.67 vs. 18.84).

TABLE 2

The reagent concentrations in ELISA and ILISA experiments are listed as the following.

| | Step | | |
|---|---|---|---|
| | 1 | 2 | 3 |
| Direct ELISA (FIG. 11) | Normal mouse IgG at designated concentrations. | Goat anti-mouse IgG HRP at 1 or 0.5 μg/mL. | ABTS solution as suggested by manufacturer. |

TABLE 2-continued

The reagent concentrations in ELISA and ILISA experiments are listed as the following.

| | Step | | |
|---|---|---|---|
| | 1 | 2 | 3 |
| Direct ILISA (FIG. 4) | Normal mouse IgG at designated concentrations. | 16.5 nm IONP with goat anti-mouse IgG antibody at 100 µg/mL. | — |
| Indirect ILISA (FIG. 5B) | Normal human IgG at 4 µg/mL. | Mouse anti-human IgG antibody at designated concentrations. | 16.5 nm IONP with goat anti-mouse IgG antibody at 100 µg/mL. |
| Competitive ILISA (FIG. 5C) | Normal mouse IgG at 4 µg/mL. | 16.5 nm IONP solution at designated concentrations. | — |
| Sandwich ILISA (FIG. 5D) | Goat anti-mouse IgG antibody at 10 µg/mL. | Normal mouse IgG at designated concentrations. | 16.5 nm IONP with goat anti-mouse IgG antibody at 100 µg/mL. |
| Sandwich ILISA (FIG. 6B) | Rabbit anti-mouse IgG antibody at 10 µg/mL. | Normal mouse IgG at designated concentrations. | 1) 16.5 nm IONP with goat anti-mouse IgG antibody at 100 µg/mL. 2) 28.8 nm IONP with goat anti-mouse IgG antibody at 200 µg/mL. 3) 16.5 nm IONP with goat anti-mouse IgG antibody at 100 µg/mL followed by 28.8 nm IONP with rabbit anti-goat IgG antibody at 200 µg/mL. |
| Sandwich ILISA (FIG. 7A) | Mouse anti-human VCAM-1 antibody at 10 µg/mL. | HUVEC protein extract at designated concentrations | 16.5 nm IONP with goat-anti human VCAM-1 antibody at 100 µg/mL. |
| Sandwich ILISA (FIG. 7B) | Rabbit anti-human Factor X antibody at 10 µg/mL. | Human Factor X deficient plasma supplemented with Factor X at designated quantities. (Plasma was diluted 1:40) | 16.5 nm IONP with rabbit-anti human Factor X antibody at 100 µg/mL. |

Example 9: IONP-Based Detection in Complex Biological Specimens

Figure 7A:
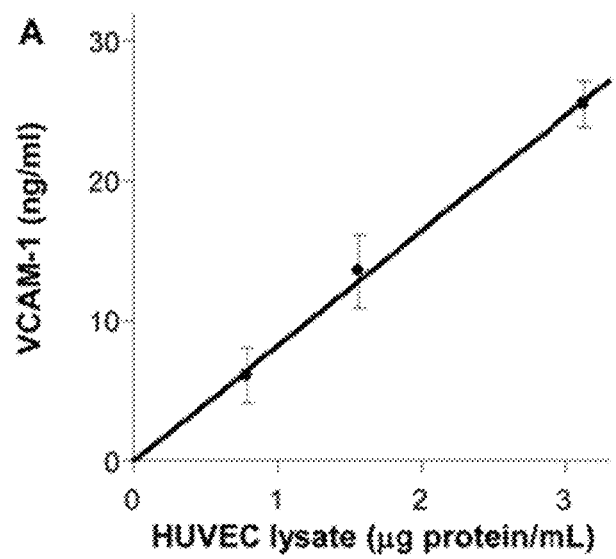
FIG. 7A is a graph of the results of sandwich ILISA, showing quantity of VCAM-1 (ng/ml) against quantity of LPS-stimulated HUVEC lysate (μg protein/mL); the mean±standard deviation of three measurements and a fitted line are plotted.
Figure 14:
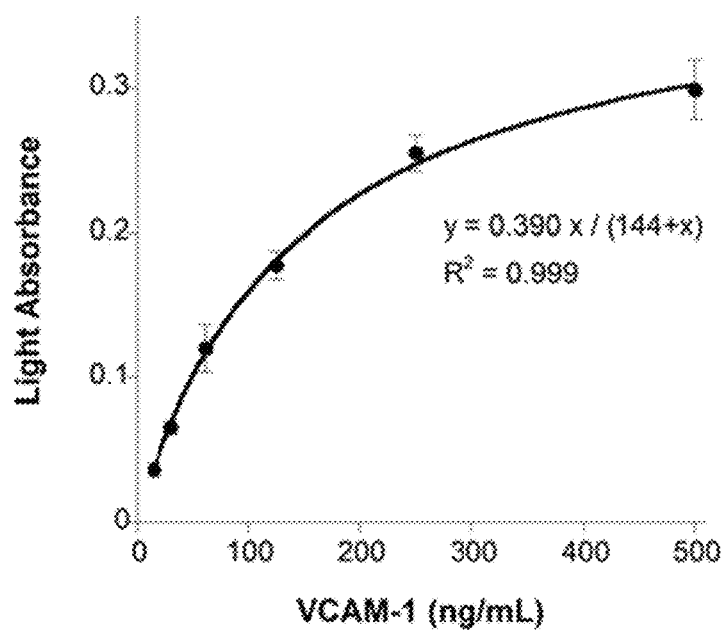
FIG. 14 is a dot plot graph showing the quantification of purified VCAM-1 measured with a sandwich ILISA. Light Absorbance is plotted against the quantity of VCAM-1 (ng/mL). The mean±standard deviation of three measurements are plotted. The curve was fitted with equation 1.

A potential issue is the interference between metal ions/chelators with iron-ferrozine chelation, especially when biological specimens are used. However, we found that sandwich ILISA could be performed with cell homogenate and plasma, the two most common types of biological samples, without special handling. This indicates that routine capture and wash steps in a bioassay can effectively eliminate interfering compounds. Specifically, human umbilical vascular endothelial cells (HUVEC) were cultured with M199 medium containing $Ca^{2+}$, $Fe^{3+}$ and $Mg^{2+}$. Vascular cell adhesion molecule-1 (VCAM-1), an inflammatory marker, could be detected by sandwich ILISA in the lysate of lipopolysaccharide (LPS)-stimulated HUVECs at low total protein concentration (1 µg/mL) while achieving a good linearity (FIG. 7A and FIG. 14).

Figure 7B:
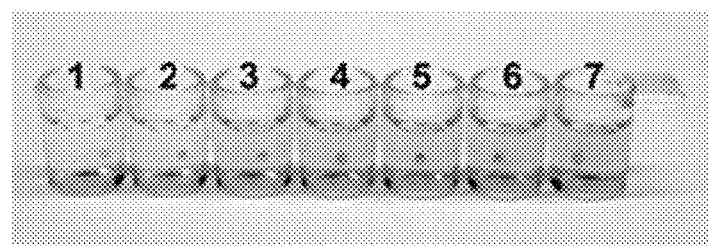
FIG. 7B is an image of seven wells (1-7) from a 96-well microtiter plate, containing samples as indicated by the legend, to demonstrate the instrument-free distinction of factor-X deficient vs. normal human plasma; factor X in human plasma was detected with a sandwich ILISA.
Figure 15:
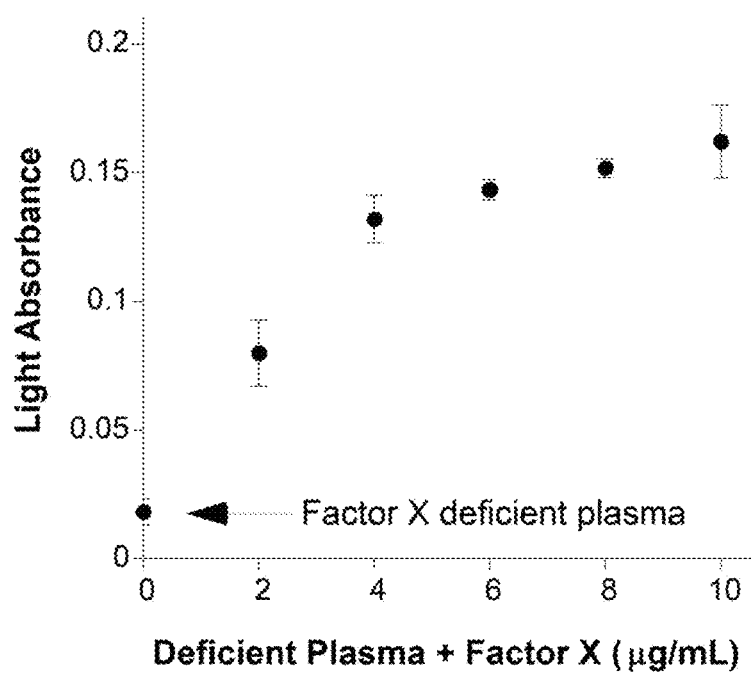
FIG. 15 is a dot plot graph showing the results of a sandwich ILISA to quantify human factor X in commercial human plasma samples. Light Absorbance is plotted against the quantity of Deficient Plasma+Factor X (μg/mL). The mean±standard deviation of three measurements is plotted.

Sandwich ILISA could also detect factor-X, a blood coagulation factor that is screened clinically for inherited or acquired factor X deficiency, in clinical plasma samples (FIG. 15). Importantly, with optimized sample dilution, the difference between a factor X-deficient patient and a healthy individual could be distinguished with the naked eye (FIG. 7B).

Figure 8A:
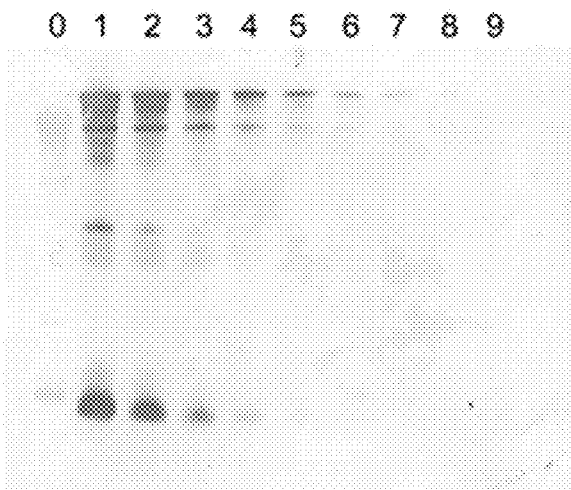
FIGS. 8A and 8B are images of a Western blot (8A) detected with 16.5 nm IONPs conjugated with rabbit anti-mouse IgG polyclonal antibody, and SDSPAGE gel (8B) stained with coomassie blue, respectively, showing lanes containing molecular weight markers (lane 0), BSA (lane 9), or mouse IgG at 4000 ng (lane 1), 2000 ng (lane 2), 1000 ng (lane 3), 500 ng (lane 4), 250 ng (lane 5), 125 ng (lane 6), 62.5 ng (lane 7) and 31.25 ng (lane 8).
Figure 8B:
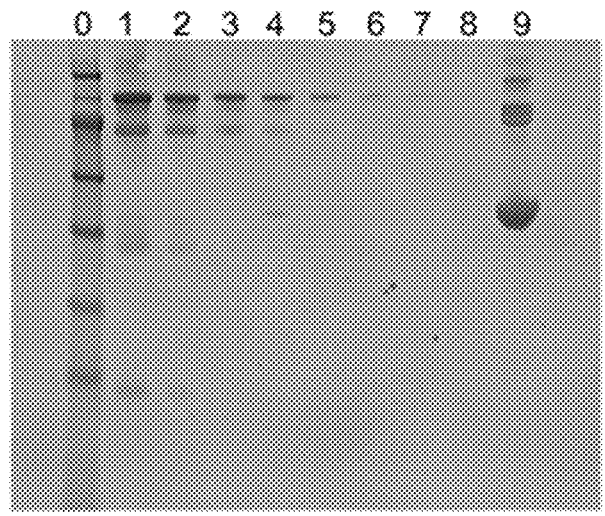

Example 10: Nanocrystal Amplification in Surface-Based Detection—Western Blot In blotting assays, biomolecules such as proteins and nucleic acids distributed on a membrane needs to be localized and detected quantitatively. As mentioned above, Prussian blue staining allows in situ detection of IONPs bound on a surface. As an example, a western blot was performed for mouse IgG at designated quantities. Bovine serum albumin (BSA) was used as the negative control. After the proteins were transferred onto a cellulose membrane, mouse IgG was detected with 16.5 nm IONPs conjugated with a rabbit anti-mouse IgG antibody (FIG. 8A). The protein bands were visualized by simply incubating the membrane in a solution containing HCl and potassium ferrocyanide. All fragments of mouse IgG can be observed because of the polyclonal nature of the detection antibody. The intensity of the bands correlated well with the quantities of mouse IgG. Mouse IgG was detected at an amount of 31 ng or 0.21 pmol, while BSA was visible with the non-specific coomassie blue staining but not with the IONPs (FIGS. 8A and 8B). Similar to ILISA, the detection sensitivity of IONPs can be further improved by using large nanoparticles or combinations of nanoparticles. Therefore, IONPs are capable of highly specific, sensitive and semi-quantitative detection on cellulose membranes.

Example 11: Distribution and Stability of Maleimide Groups on IONPs

The distribution and stability of maleimide groups on IONPs were examined with gel electrophoresis. Hydrolyzed maleimide becomes negatively charged maleic acid; whereas active maleimide can react with 2-mercaptoethylamine (MBA) that has a positively charged amine. The IONPs with and without active maleimide groups can be distinguished in gel electrophoresis following MBA reaction. IONPs formed of 6.5 nm wüstite nanocrystals have better mobility in agarose gel than the larger ones and were used in this study. The wüstite nanocrystals were coated with DSPE-mPEG and DSPE-PEG-maleimide as described in Methods. After that, the IONPs were stored in cold deionized water for 90 minutes, 5 hours, 24 hours and 48 hours before reacting with MEA in PBS. In the control group, the IONPs were incubated in PBS overnight so that all maleimide groups were hydrolyzed. Electrophoresis was performed in 0.5% agarose gel (135V, tris-acetate-EDTA buffer, pH 8.3 and 45 minutes). All IONPs reacted with MEA were clearly separated from the control group, proving availability of active maleimide on functionalized IONPs stored for at least 48 hours in cold deionized water (FIG. 9). The narrow bands suggest the uniform distribution of maleimide among IONPs.

Example 12: Binding Avidity of Antibody-Conjugated IONPs

Figure 10:
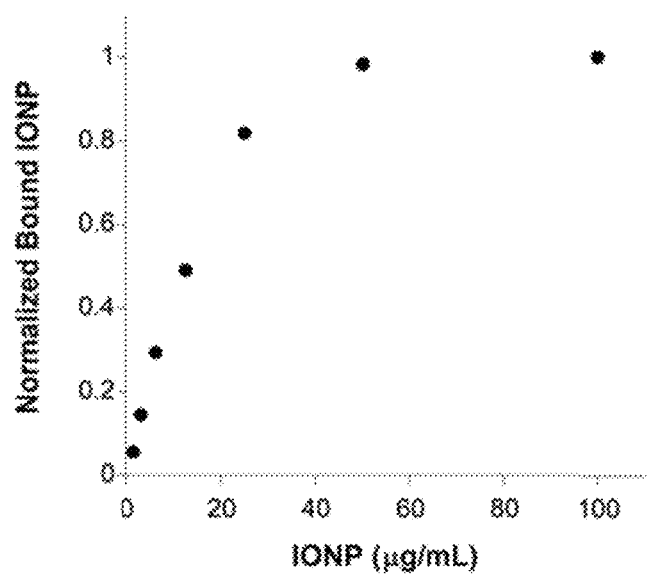
FIG. 10 is a dot plot graph showing the binding avidity of 16.5 nm IONPs conjugated with goat polyclonal antibody, examined by titration in a direct ILISA. Amounts of bound IONPs, normalized by the value obtained with 100 μg/mL IONP, are plotted against the initial concentration of IONP (μg/mL); the mean±standard deviation of three measurements is plotted. Error bars are not plotted due to minimal variations in the measurements.

The binding avidity of 16.5 nm IONPs conjugated with goat polyclonal antibody were examined by titration in a direct ILISA. The plate was coated with 2 µg/mL mouse IgG and blocked with 1% BSA. The wells were incubated with IONPs at designated concentrations. The amount of bound IONPs reached a plateau when the wells were incubated with 50 µg/mL IONPs (FIG. 10). The IONP concentration required to reach half of the saturation level was 12.5 µg/mL or 1.99 nM. To ensure sufficient binding, the loading concentration of the 16.5 nm IONPs was fixed at 100 µg/mL in all ILISA experiments unless other specified.

Example 13: Direct ELISA

Figure 11A:
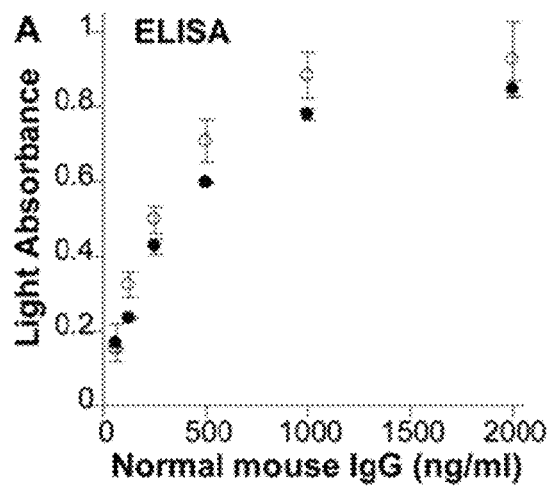
FIGS. 11A and 11B show the results of a direct ELISA, whereby a 96-well microtiter plate was coated with normal mouse IgG at designated concentrations and surface bound mouse IgG was detected with a goat anti-mouse IgG polyclonal antibody conjugated to HRP.
Figure 11B:
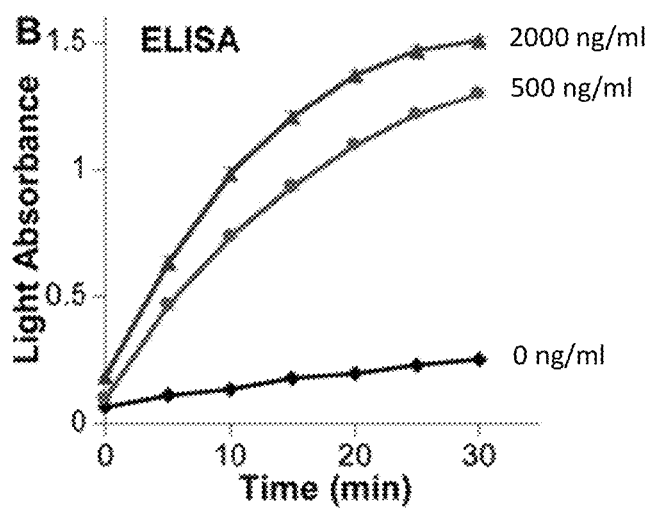

The results from a direct ELISA were provided for comparison with the direct ILISA. All reagents concentrations in the direct ELISA were the same as those in the direct ILISA, except that surface-adsorbed analyte was detected with a complex of antibody and horseradish peroxidase (HRP) (Table 2). There was no linear correlation between optical reading and analyte concentration prior to tedious optimization (FIG. 11A). Further, light absorbance was sensitive to variations in antibody/HRP concentration and incubation time, a typical feature of nonlinear and volatile enzyme catalysis (FIG. 11B).

Example 14: Steric Hindrance in Immunosorbent Assays

Figure 12:
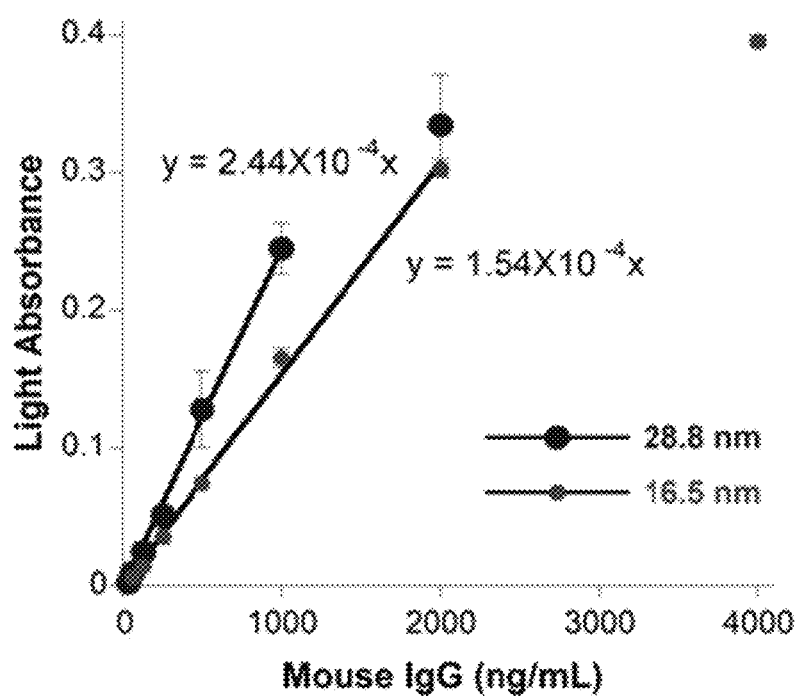
FIG. 12 is a dot plot graph showing detection sensitivity of 28.8 nm IONPs (large dots) and 16.5 nm IONPs (small dots) in direct ILISA. For each series, linear values for Light Absorbance are plotted against linear values for quantity of Mouse IgG (ng/mL). The mean±standard deviation of three measurements and a fitted line is plotted; within the linear range of the direct ILISA, the detection sensitivity of 28.8 nm IONPs, as indicated by the slope of fitted line, was only 58% higher than that of 16.5 nm IONPs.

In immunosorbent assays, the measurements saturate at high analyte concentrations due to steric hindrance. To elucidate the source of steric hindrance, we compared protein detection with 16.5 nm and 28.8 nm IONPs in direct ILISA and sandwich ILISA. Within the linear range of the direct ILISA, the detection sensitivity of 28.8 nm IONPs, as indicated by the slope of fitted line, was only 58% higher than that of 16.5 nm IONPs (FIG. 12). The increase in detection sensitivity was less than the volume ratio of these IONPs, indicating many proteins were only detectable with the smaller probe. This is probably due to the arbitrary molecular orientation on the plate surface. The epitopes on some molecules may become less accessible for larger nanoparticles. On the other hand, the detection sensitivity of the same IONPs was 3 times higher in the sandwich ILISA (FIG. 5D) than that in the direct ILISA. Furthermore, the detection sensitivity of different IONPs in sandwich assays was in good agreement with the crystal size (FIG. 6B). The discrepancy between the direct and the sandwich assays is attributable to the fact that the target proteins were lifted by capture antibodies from the plate surface, improving the probe accessibility.

Another type of steric hindrance arises from the overcrowding of target molecules on the surface. As shown in FIG. 12, the saturation concentration of 28.8 nm IONPs was lower than that of 16.5 nm IONPs. Therefore, the top detection limit of ILISA is determined by the inter-molecule distance between target molecules.

Example 15: Signal Amplification in Sandwich ILISA

Linear plots of FIG. 6B are shown in FIG. 13. The detection sensitivity of the three assays can be evaluated by the slope of fitted lines.

Example 16: Quantification of Cellular VCAM-1

HUVEC was cultured according to vendor's instructions. When the cells reached 80~90% confluence, the cells were incubated with media containing 100 ng/mL LPS overnight. After incubation, cell lysate was then prepared with RIPA buffer and the total protein concentration was measured with a coomassie brilliant blue G-250 dye (Bradford protein assay kit, Bio-Rad). VCAM-1 in the cell lysate was measured with a sandwich ILISA (Table 2). Standard curve of VCAM-1 was created with recombinant human VCAM-1 (FIG. 14). The curve was fitted with Equation 1.

Example 17: Quantification of Human Factor X

Figure 4E:
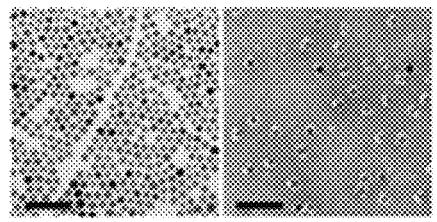
FIG. 4E is a dot plot graph showing results of three independent measurements of mouse IgG using direct ILISA, carried out as in (4C). For each assay, IONP quantity (fmol) is plotted against Normal Mouse IgG quantity (ng/ml); the mean±standard deviation of three measurements is plotted.
Figure 4E:
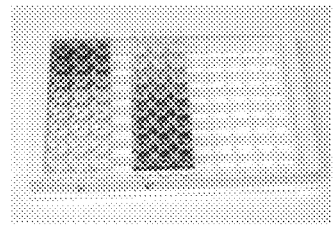
Figure 4E:
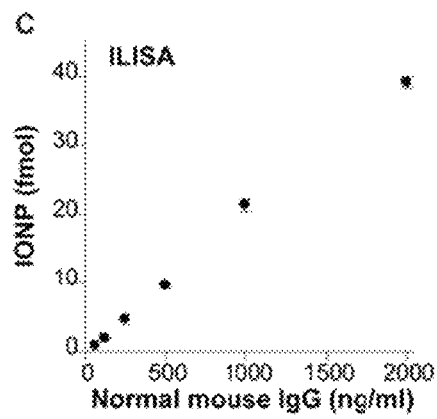
Figure 4E:
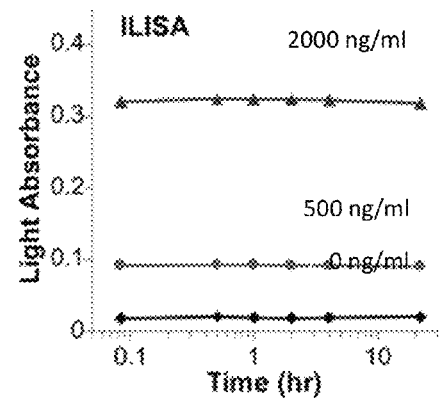
Figure 4E:
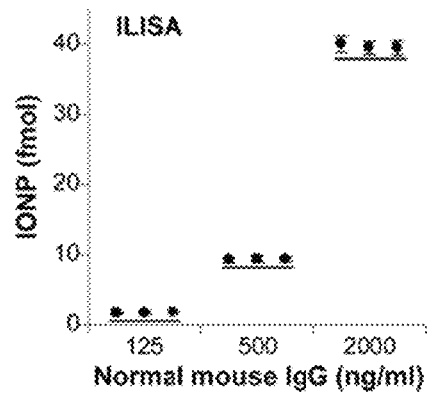
Figure 5A:
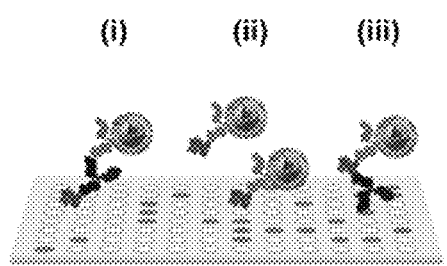
FIG. 5A is a schematic diagram of the application of IONPs in major forms of immunosorbent assays; indirect (i), competitive (ii) and sandwich (iii) ILISA.
Figure 5B:
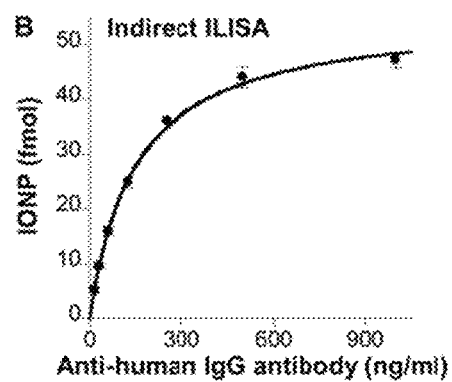
FIGS. 5B, 5C and 5D are dot plot graphs showing results of Indirect ILISA, Competitive ILISA and Sandwich ILISA, respectively, performed with 16.5 nm IONPs conjugated with goat anti-mouse IgG antibody. Quantity of IONP (fmol) is plotted against quantity of Anti-human IgG antibody (ng/mol) (FIG. 5B) and Normal Mouse IgG (FIGS. 5C and 5D); the mean±standard deviation of three measurements was plotted. The curve in FIG. 5B was fitted with Equation 1.
Figure 5C:
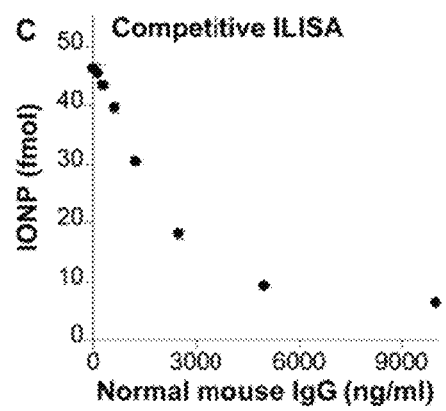
Figure 5D:
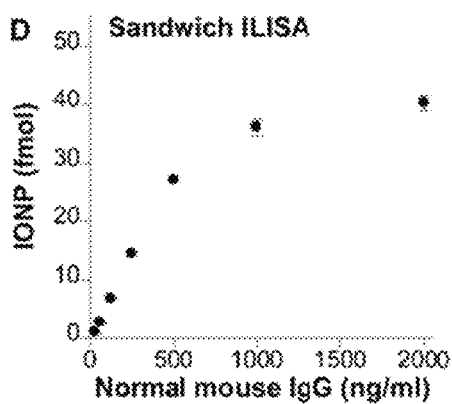

Factor X in commercial human plasma samples was measured with a sandwich ILISA (Table 2 and FIG. 15). In brief, human factor X deficient plasma was stored at −80° C. Before performing ILISA, the plasma was thawed at room temperature and inactivated by incubating at 56° C. for 1 hour to block enzymatic degradation of factor X due to coagulation reaction. Designated amount of human factor X was added to the factor X deficient plasma. Deficient plasma plus 10 µg/mL human factor X protein was used as normal plasma. The plasma samples were diluted 1:40 with PBS so that the light absorbance saturated at the middle point between factor X deficient vs. healthy plasma. FIG. 4B shows the picture of color-developed sample strips corresponding to the data in FIG. 15.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:
1. A detection agent comprising:
  a metal or metal oxide nanocrystal conjugated to a binding moiety that specifically binds to a target, wherein the metal or metal oxide nanocrystals are free of inter-particle magnetic interactions, wherein metals or metal oxide nanocrystals exhibit metal-induced chromogenesis, and are dissolvable in acids, and wherein the metal or metal oxide nanocrystals are wüstite nanocrytals having a diameter of 10-50 nm.
2. The detection agent of claim 1, wherein the nanocrystal is coated with a polymer.

3. The detection agent of claim 2, wherein the polymer comprises 1,2-Distearoyl-sn-glycero-3-phosphoethanolamine-N-[methoxy (polyethylene glycol)-2000] (DSPE-mPEG), 1,2-distearoyl-sn-glycero-3-phosphoethanolamine-N-[maleimide (polyethylene glycol)-2000] (DSPE-PEG-maleimide) or a combination thereof.

4. The detection agent of claim 1, wherein the binding moiety is selected from the group consisting of an aptamer, antibody, lipid, protein, peptide, and carbohydrate.

5. The detection agent of claim 1, wherein the detection agent is attached to a substrate.

6. The detection agent of claim 5, wherein the substrate is a planar substrate or a culture dish.

7. A solid support comprising the detection agent of claim 1 immobilized on the solid support.

8. The solid support of claim 7, wherein the solid support is selected from the group consisting of a microtiter plate, a dipstick, nitrocellulose, beads, and culture dish.

9. A kit comprising the detection agent of claim 1 and reagents for performing a chromatogenic reaction induced by metal atoms of the nanocrystal.

10. The detection of claim 1, wherein the wüstite nanocrystals have a diameter of 16.5 nm to 28.8 nm.

11. A detection agent comprising:
    wüstite nanocrytals having a diameter of 10-50 nm wherein the wüstite nanocrytals are coated with a polymer.

12. The detection agent of claim 11, wherein the polymer comprises 1,2-Distearoyl-sn-glycero-3-phosphoethanolamine-N-[methoxy (polyethylene glycol)-2000] (DSPE-mPEG), 1,2-distearoyl-sn-glycero-3-phosphoethanolamine-N-[maleimide (polyethylene glycol)-2000] (DSPE-PEG-maleimide) or a combination thereof.

* * * * *